United States Patent [19]

Meyer et al.

[11] 4,058,730
[45] Nov. 15, 1977

[54] IRRADIATING DEVICE WITH AN ELECTRONIC ACCELERATOR

[75] Inventors: Rudolf Meyer, Erlangen; Wolf-Eberhard Schiegl, Weisendorf; Leonhard Taumann, Erlangen, all of Germany

[73] Assignee: Siemens Aktiengesellschaft, Munich, Germany

[21] Appl. No.: 666,233

[22] Filed: Mar. 12, 1976

Related U.S. Application Data

[63] Continuation-in-part of Ser. No. 506,327, Sept. 12, 1974, abandoned.

[51] Int. Cl.² .................................................. G01T 1/29
[52] U.S. Cl. .................................. 250/397; 250/305; 250/385
[58] Field of Search ................ 250/305, 336, 397, 385

[56] References Cited

U.S. PATENT DOCUMENTS

| 3,293,429 | 12/1966 | Leboutet et al. | 250/397 X |
| 3,626,184 | 12/1971 | Crewe | 250/305 |
| 3,808,441 | 4/1974 | Boux | 250/397 |

Primary Examiner—Archie R. Borchelt
Attorney, Agent, or Firm—Allison C. Collard

[57] ABSTRACT

An irradiating device has an electronic accelerator, an actuating and monitoring device, means for expanding and homogenizing the electronic ray with respect to electron density and a diaphragm for side limiting the electronic beam. The invention is particularly characterized by the provision of a measuring device containing several radiation detectors connected to the actuating and monitoring device for increasing the operational safety of the irradiating device and located in the electronic beam in the ray direction behind the means for expanding and homogenizing the electronic beam. At least the first of these radiation detectors is located in the angular space range of the unscattered electronic ray.

9 Claims, 5 Drawing Figures

IRRADIATING DEVICE WITH AN ELECTRONIC ACCELERATOR

This application is a continuation-in-part of a copending patent application, Ser. No. 506,327, filed Sept. 12, 1974, and now abaondoned.

This invention relates to an irradiating device with an electronic accelerator, an actuating and monitoring device, means for expanding and homogenizing the electronic ray with respect to electron density and a diaphragm for side limiting the electronic beams.

Irradiating devices are known, particularly in medical technology, wherein electronic accelerators, mostly betatrons, more rarely lineal accelerators, are used for irradiation with highly energetic electrons. Electrons beams leaving the accelerating tubes of electronic accelerators have cross sections which are too small as compared to surfaces which are usually irradiated in medical technology. Thus an electronic beam leaving the accelerating tube of a linear accelerator has a diameter a little greater than 1mm. An electronic beam emerging from the accelerating tube of a betatron has a line-shaped cross section with a width somewhat greater than 1mm and a length in the plane of its theoretical circle in the accelerating tube of about 10mm. In both electronic accelerators the divergence of the electronic beam is symmetrical to the axis of the electronic beam. It amounts to about 1°. Furthermore, the beam density, is very greatly reduced transversely to the beam direction. Thus, these electronic beams leaving the accelerating tubes are not suitable for irradiating large surface areas, particularly since the medical technology has the requirement that equal amounts of rays must be applied to specifically defined limited surfaces ranges for each surface element.

It is known in the art that a uniform irradiating larger surface areas may be provided by widening the electronic ray homogenizing/and/the electron density leaving the accelerating tube of an electronic accelerator. For that purpose, for example, scattering foils adapted in their thickness to the electronic energy are arranged in the path of electrons leaving the accelerating tube. Electrons are scattered out of their original direction by statistically distributed small angles at the molecules of the scattering foils. This makes wider the ray beam, namely, the divergence of the beam is increased. Furthermore, the scattering at the molecules of the scattering foils balances local lacks of uniformity of the electronic density in the electronic beam, or, in other words, the dose output which is to be applied, is homogenized behind the scattering foils. At a distance of 1 to 2 meters from the scattering foils the electronic beam widened in such manner can uniformly irradiate areas of about one square decimeter. It can happen, however, that the device used for transporting scattering foils adapted to the selected electronic energy in front of the outlet window of the accelerating tube, becomes defective, and then radiation takes place with an electronic beam which electron density was not homogenized, or was insufficiently homogenized, or in an extreme case not sufficiently scattered. In that case locally increased and in other locations again strongly reduced dose rates are applied.

German specification No. 2,218,237 describes a safety system for such irradiating devices wherein two ionization chambers containing the entire electronic beam are located one behind the other in the ray direction. These ionization chambers switch off the irradiating device when, even in one of these chambers, the ray dose permissible therein has been applied. Since there are two ionization chambers connected one behind the other, this system continues to function even when one ionization chamber drops off. Due to the subdivision of the second ionization chamber into four segments this ionization chamber can also control its centering to the electronic beam. However, this safety system has the drawback that it is not possible to notice radiations with a not extended or not sufficiently electron density homogenized electronic ray. Thus, despite the automatic switching off, there is the possibility that locally super-high ray doses will be applied.

An object of the present invention is to increase operational safety of irradiating devices which use electronic accelerators, particularly, however, to locate zones of law electron density and homogeneity in electronic beams and to prevent the application of locally super-high ray doses.

Other objects of the present invention will become apparent in the course of the following specification.

In the accomplishment of the objectives of the present invention the irradiating device of the described type creates an increase in the operational safety of the device by providing for the electronic beam in ray direction behind means expanding and electron density homogenizing the electronic beam, a measuring device containing several radiation detectors and connected to the actuating and monitoring device. The first of these radiation detectors as far as its length and measurements are concerned is adapted only to the angular range of the unscattered electronic beam. This angular range has in case of a betatron a narrow rectangular cross-section and in case of all other electronic accelerators a round cross-section. By the use of a radiation detector adapted to the angular range of the unscattered electronic beam measuring values are obtained which in case there is no scattering of the electronic beam or when there is insufficient electron density homogenizing of the electronic beam, irrespective of the cause, are greater than in case of an electronic beam which is properly scattered and electron density homogenized. Thus the measuring values of this radiation detector are particularly suitable in combination with other ray detectors for supervising the electron density homogenizing extent of the ray beam as well as the correct location and the proper condition of scattering foils.

According to a further advantageous embodiment of the present invention the radiation detectors, with the exception of the first radiation detector, can be made the same in construction and are arranged in a plane perpendicular to the unscattered electronic ray and symmetrically thereto. In such an arrangement and construction of the other ray detectors their outgoing signals must be always equal to each other for an electron density homogenized electronic ray. Thus they can be particularly easily compared with each other in the actuating and monitoring device and are therefore well suited for controlling the electron density homogeneity of the electronic beam.

According to a further useful embodiment of the present invention, when a betatron is used the first radiation detector can be arranged in a plane perpendicular to the unscattered electronic ray extending along the plane of the theoretical circular path of the accelerating portion of the electronic ray. In case of betatrons, the electrons are ejected sun-wheel shaped from their theoretical circular path by a local magnetic interference field. For that reason, the electronic beam leaving the accelerating tube is widened line-like in the plane of the theoretical circle. Due to this described construction of the present invention the first radiation detector is exposed to the entire cross-section of an electronic beam which possibly leaves undispersed the accelerating tube. It can therefore obtain a size sufficient for producing an adequate measuring sensibility.

According to yet another advantageous embodiment of the present invention the radiation detectors, with the exception of the first ray detector, when using a betatron, can be located in a plane perdendicular to the unscattered electronic ray, symmetrically thereto and with the same surface sections divided at both sides of the plane of the theoretical circular path of the acceleration portion of the electronic beam. Since the outgoing electronic beam in case of a betatron is widened line-like in the plane of the theoretical path, only such arrangements of radiation detectors which extend with equal surface sections at both sides of the plane of the theoretical path will provide information about the sufficient homogenizing of the electronic ray with respect to electron density. Of importance is here also the ratio of the dose per surface unit of the first ray detector located in the theoretical circular plane to the dose per surface unit of those ray detectors which are located on both sides of the theoretical circular plane. This also applies to other electronic accelerators wherein ray detectors also located in diametrically opposed ranges of the beam better provide information about sufficient electron density homogenizing in beam cross-section.

The invention will appear more clearly from the following detailed description when taken in connection with the accompanying drawings showing, by way of example only, preferred embodiments of the inventive idea.

Figure 1:
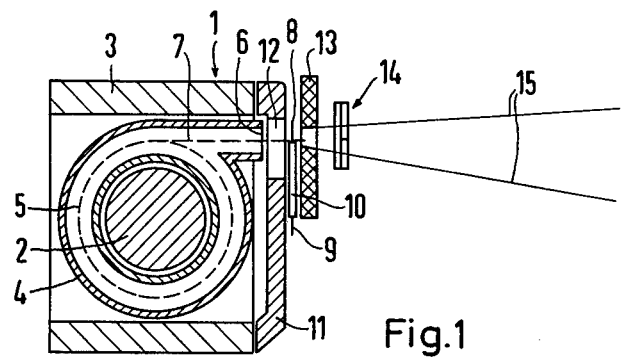
FIG. 1 is a section through an irradiating device with a betatron.

FIG. 1 shows in section a betatron 1. An accelerating tube 4 is shown as being located between the poles 2 of an electromagnet 3. A theoretical circular path 5 is indicated by broken lines within the accelerating tube upon which the electrons are held and accelerated by the magnetic field. The accelerated electrons are directed to the outside through a window 6 of the accelerating tube 4 by a deflector which is known in the art and is not illustrated. A scattering foil 8 is located in the path of this electronic beam 7 directly in front of the window 6 of the accelerating tube. The foil 8 along with other scattering foils 9 is fixed upon the circumference of a wheel-like rotary member 10. An opening 12 is provided in the radiation shield 11 constituting a collimator in the ray direction behind the scattering foil positioned in front of the window, for the passage of electrons. Behind this opening is located an adjustable radiation screen or collimator 13. Behind the collimator and in the beam direction a measuring device 14 containing several beam detectors is located in the electron cone 15 defined by the electron beam.

Figure 2:
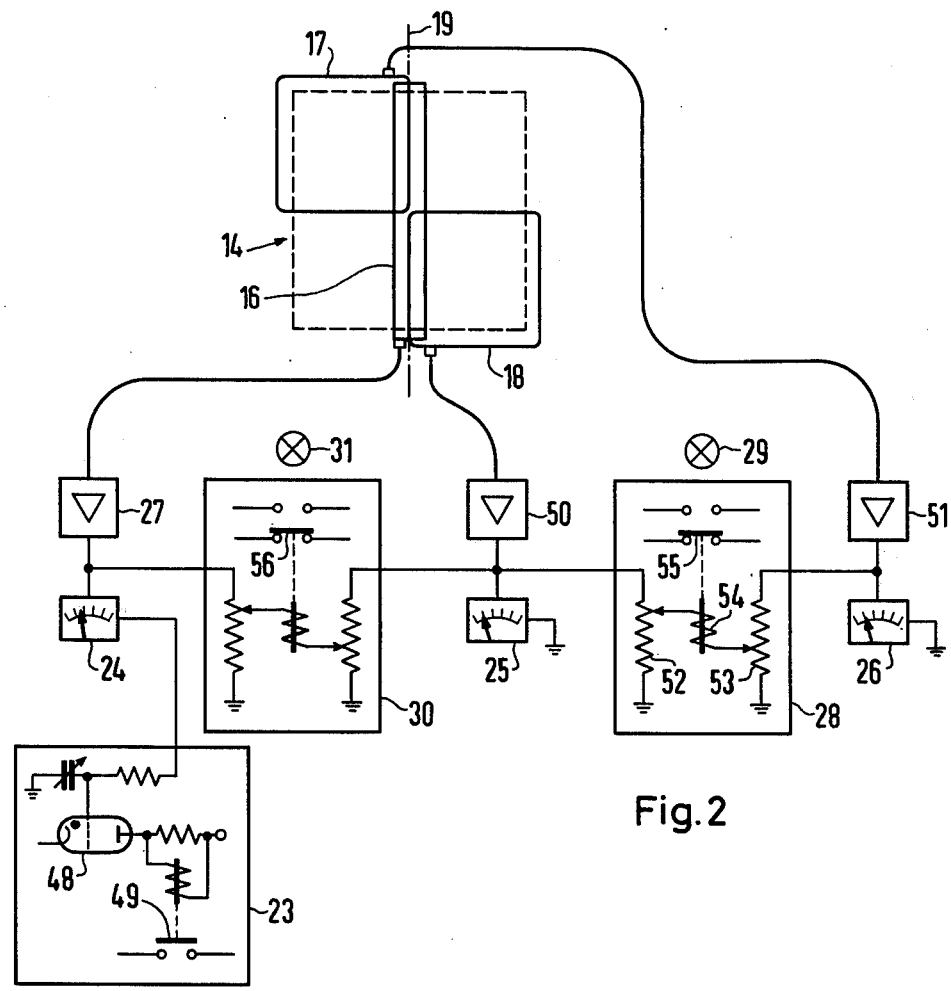
FIG. 2 shows diagrammatically the measuring device with the ray detectors in the viewing direction opposed to the beam direction, as well as the connections of the ray detectors to electrical structural elements.

The upper portion of FIG. 2 shows this measuring device 14 is a viewing direction opposed to the beam direction. It is shown that the measuring device consists of three detectors 16, 17 and 18. These detectors which should absorb the smallest amount of rays, have been long known in the art as ionization chambers. They are flat closed casings filled with a easily ionizable gas (see U.S. Pat. No. 1,858,537, sec. 7). The two opposed larger wall elements are constructed as electrodes. A constant electrical direct voltage is applied to these electrodes. The current between the two electrodes is proportional to the intensity of the ionized beaming. Of these detectors, the detector 16 extends along the plane 19 of the theoretical circular path 5 of the beam in the accelerating tube 4. It is substantially as wide as the non-strayed beam. The two other detectors 17, 18 are arranged by equal surface parts on both sides of this plane. These detectors 17, 18 located on both sides of the plane of the theoretical circular path are always close to the opposed ends of the detector 16 extending in the plane of the theoretical circular path 19. The greatest scatterable ray cone is shown by broken lines in FIG. 2.

Figure 3:
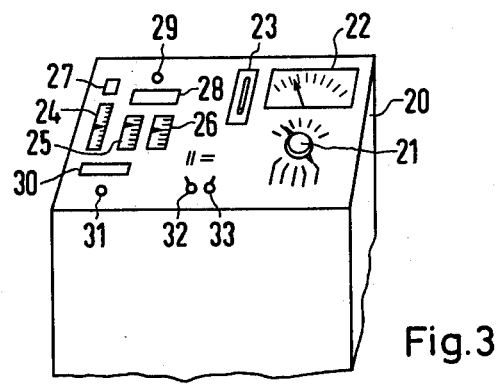
FIG. 3 is a perspective view of the actuating and monitoring device of the irradiating device.

FIG. 3 shows in partial perspective a servicing console 20 for the radiating device having a selection switch 21 for the energy of the electrons with which, at the same time, the scattering foil pertaining to that particular energy is also pre-selected, as indicating device 22 for the strength of the current, a switch off automat 23, as well as three indicating instruments 24, 25 and 26 for the ray doses measured by the three detectors 16, 17 and 18.

The lower portion of FIG. 2 shows connections of the detectors to the indicating instruments and other structual parts of the servicing console. An amplifier 27 is connected in front of the indicating instrument 24 for the detector 16 which is set for the angular space range of the unscattered beam. To the amplifier 27 is also connected the switch off automat 23 for the radiating device. This switch off automat is known in prior art from U.S. Pat. No. 2,909,666. There the voltage at the capacity 54 also increases until the gas discharging tube 43 is ignited. In the present embodiment the coil of a relay 49 is switched in the current circuit of the gas discharge tube 48, by means of which the current supply of the illuminating device, in this case betatron 1, is interrupted. The indicating instruments 25, 26 provided for the two other detectors 17, 18 are connected by amplifiers 50, 51 to the two inlets of a differential amplifier 28. Such an amplifier is disclosed in prior art, namely, in U.S. Pat. No. 3,345,516 by numeral 56 and in the U.S. Pat. No. 2,913,582 by numeral 40. However, in the amplifier of this embodiment the current measuring devices 25, 26 and the differential amplifiers 28, 30 are connected in the X-ray tube current circuit, instead of the winding 48 of U.S. Pat. No. 2,913,582. The differential amplifier includes two voltage divider 52, 53, connected to separate inlets of the differential amplifier. The winding 54 of a relay 55 is connected between their contacts. This switches on an optical signalling device 29. Furthermore, the inlet of another similar differential amplifier 30 is connected parallel to the indicating instrument 25. To the other inlet of the amplifier is connected the amplifier 27 for the ray detector 16 extending in the plane of the theoretical circular path. This differential amplifier also connects an optical signal transmitter 31. The operational console also carries the two setting members 32, 33 for adjusting the radiation collimator 13 (FIG. 1).

Before starting the irradiation, the doctor will set with the setting members 32 and 33, the desired opening of the radiation collimator 13 and thus the field to be radiated. If, thereupon, he selects with the rotary button 21 a specific electronic energy, this button will determine at the same time a corresponding scattering foil 8, 9 adapted to this electronic energy. The rotary member 10 (FIG. 1) with the scattering foils is rotated by a motor steering (not shown) until the corresponding scattering foil will be located in front of the outlet window 6 of the accelerating tube 4. During the irradiation, the radiation doses measured by the individual detectors 16, 17, 18 of the measuring device 14 are indicated by their corresponding indicating instruments 24, 25, 26. As soon as the ray detector 16 of smaller area has measured a radiation dose preliminarily set at the variable capacity of the switch off automat, the switch off automat 23 is released and the radiation is terminated. The arrangement of the first detector 16 in the annular space section which would be filled by the non-scattering electron ray, provides that the radiation in the case of an insufficient scattering of the electron beam is switched off prematurely in the range of the irradiated field due to the higher dose output flowing to this radiation detector 16, namely, when the preset ray dose is reached, which otherwise would receive the highest dose. The two other detectors 17, 18 arranged segment-like, must produce equal measured values for a sufficiently homogenized electron beam since they have equal surfaces. Due to the arrangement of the two ray detectors 17, 18 at the two opposed ends of the first detector 16 located at the theoretic circular plane 19, the homogeneity of the strayed rays along this theoretical circular plane is controlled at the same time. If the electron beam density is not homogenous, or if the screen opening is not symmetrical relatively to the two detectors 17, 18, their measured values will deviate from each other. The actuation of the differential amplifier 28 connected with the two detectors, and of the optical signal transmitter 29 connected thereto, is thus an indication for an incorrectly introduced scattering foil or for a non-adjusted radiation screen. However, the measured values of the first detector 16 located in the theoretical circular plane and of the two other detectors 17, 18 have a specific ratio to each other when a specific acceleration energy of electrons is selected and a scattering foil is adapted to this acceleration energy. Thus the measured value of the first detector 16 for the central beam, which was increased by the amplifier 27 in its amount by a corresponding factor, can be compared by the differential amplifier 30 also with the measured values of the two other detectors 17, 18. The optical signal transmitter 31 provided for this other differential amplifier will therefore be illuminated only when the electronic beam is greatly inhomogenous, if, for example, no scatering foil is introduced into the radiation flow or is only partially introduced.

The doctor can determine by the signal transmitters 29, 31 not only the absence of homogeneity in the electronic beam, but can also make certain conclusions about its reason. It is also possible to connect the two additional contact sets of the relay 55, 56 in series to the contact set of the switch-off automat 23. In that case, when there is insufficient homogeneity of the electron beam, the irradiating device would be switched off immediately after it was switched on, so that erroneous irradiation can not take place at all.

Figure 4:
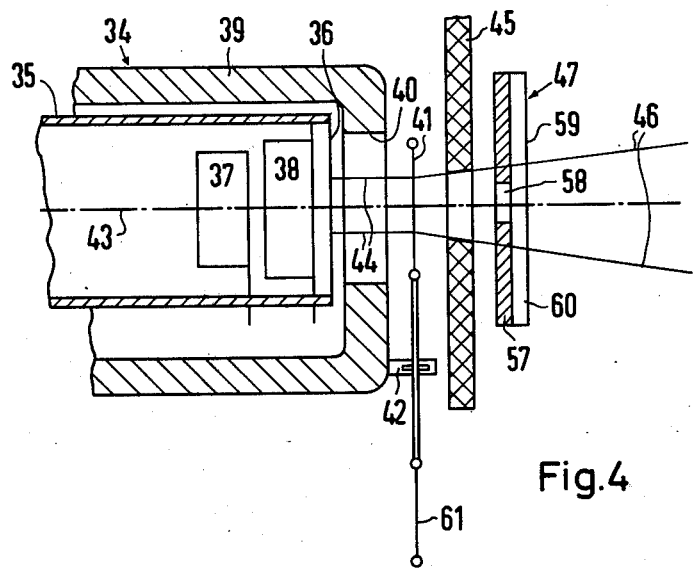
FIG. 4 is a section through a radiating device having a linear accelerator.

FIGS. 1, 2 and 3 show an embodiment of an irradiating device using a betatron 1. In the same manner it is possible to supervise an irradiating device with a linear accelerator. FIG. 4 shows an irradiating device with a linear accelerator 34. The accelerating tube 35 of the linear accelerator 34 is closed by a thin vacuum-tight outlet window 36 for the passage of accelerated electrons. In the accelerating tube 35 there are two accelerating electrodes 37, 38 extending in ray direction directly in front of the outlet window. The accelerating tube is surrounded by a radiation shield casing 39 which is provided with a break 40 for the passage of electrons located opposite the outlet window 36 of the accelerating tube. In the ray direction closely behind the outlet window 36 there is a scattering body 41 which along with several other scattering bodies 61 is swingably mounted on an axle 42 fixed to the radiation shield casing 39 and oriented parallel to the symmetry axis 43 of the accelerating tube 35. The scattering body 41 is swingable in the electron beam cone 44 leaving the accelerating tube. A radiation collimator 45 is located directly behind the scattering body 41 in the ray direction. After the radiation screen in the ray direction and in the electron beam cone 46 there is a measuring device 47 with three radiation detectors.

Figure 5:
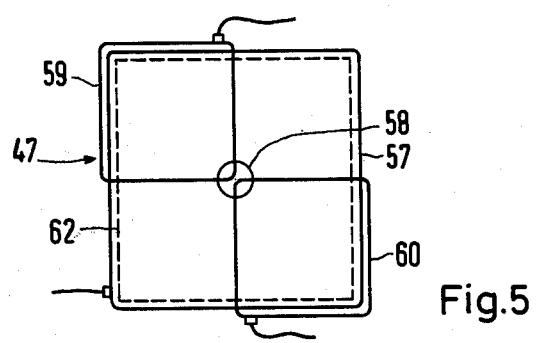
FIG. 5 shows the measuring device with ray detectors for a linear accelerator in the viewing direction opposed to the beam direction.

FIG. 5 shows the arrangement of ray detectors 57, 58, 59 in the viewing direction opposed to the beam direction. It is apparent that the detectors have the same diagonal ranges of the greatest useable beam cross-section 62, as the ray detectors 17, 18 of FIG. 2. Only the ray detectors 57 covers the entire useable beam cross-section 60. However, it is inactive by the foaming of the gas volume with the exception of a central range 58 adapted to the measures of the unscattered ray cross-section.

What is claimed is:

1. An irradiating device, comprising an electronic accelerator, an actuating and monitoring device, means for widening the electron beam and homogenizing the electron density thereof, a collimator adjacent said means for laterally limiting the electron beam, a measuring device positioned in the beam direction behind said means and connected with said actuating and monitoring device, said measuring device comprising a plurality of radiation detector means for detecting and indicating an insufficient widening and homogenization of the electron beam to thereby increase the operational safety of the irradiating device, one of said radiation detector means being disposed within the angular space range of the unscattered electron beam for measuring the electron beam solely within said range.

2. An irradiating device according to claim 1, wherein other of said radiation detector means with the exception of said one radiation detector means are equal to each other and are located in a plane perpendicular to said unscattered electron beam and symmetrically disposed relative thereto.

3. An irradiating device according to claim 1, wherein said accelerator is a betatron and wherein said one radiation detector means extends in a plane perpendicular to said unscattered electron beam along the plane of a theoretical circular path of an acceleration portion of the electron beam.

4. An irradiating device according to claim 1, wherein said accelerator is a betatron and wherein other of said radiation detector means with the exception of said one radiation detector means extend in a plane perpendicular to said unscattered electron beam and symmetrically disposed relative thereto and have equal surface parts located on both sides of a plane of the theoretical circular path of an acceleration portion of the electron beam.

5. An irradiating device according to claim 4, wherein siad other radiation detector means which are located at both sides of the plane of the theoretical circular path of the acceleration portion of the electron beam are further located close to opposite ends of an unscattered electron beam having a line-shaped cross section.

6. An irradiating device according to claim 1, wherein said radiation detector means are located behind said collimator in the direction of the beams.

7. An irradiation device according to claim 1 additionally comprising a relay mechanism coupled to said one radiation detector means and said actuating device and responsive to a signal from said detection means for terminating the radiation when it exceeds predetermined limits.

8. An irradiating device according to claim 1, comprising a differential amplifier having two inlets and an outlet, said one radiation detector means being connected to one of said inlets, the other radiation detector means being connected to the other inlet, other amplifier means connected with one of said inlets for varying the measured values in a ratio adapted to preselected electron energy and indicating means connected to said outlet.

9. An irradiating device according to claim 5, wherein the other radiation detector means include two radiation detectors located opposite each other, the device further comprising a differential amplifier connected with said two radiation detectors, and a separate indicating device connected with said differential amplifier.

* * * * *